(12) United States Patent
Lai et al.

(10) Patent No.: US 10,358,417 B2
(45) Date of Patent: Jul. 23, 2019

(54) METHOD FOR PREPARING EFFICIENTLY SYNTHETIC SITAFLOXACIN INTERMEDIATE (7S)-5-AZASPIRO[2.4]HEPTANE-7-YL TERT-BUTYL CARBAMATE

(71) Applicant: Chen-Stone (Guangzhou) Co., Ltd., Guangdong (CN)

(72) Inventors: Yingjie Lai, Guangdong (CN); Dabing Ye, Guangdong (CN); Fengrui Lang, Guangdong (CN); Xiangtian Long, Guangdong (CN)

(73) Assignee: Chen-Stone (Guangzhou) Co., Ltd., Guangdong (CN)

( * ) Notice: Subject to any disclaimer, the term of this patent is extended or adjusted under 35 U.S.C. 154(b) by 0 days.

(21) Appl. No.: 16/062,846

(22) PCT Filed: Apr. 25, 2017

(86) PCT No.: PCT/CN2017/081893
§ 371 (c)(1),
(2) Date: Jun. 15, 2018

(87) PCT Pub. No.: WO2017/190609
PCT Pub. Date: Nov. 9, 2017

(65) Prior Publication Data
US 2018/0370914 A1    Dec. 27, 2018

(30) Foreign Application Priority Data

May 6, 2016 (CN) ............. 2016 1 0301567

(51) Int. Cl.
*C07D 209/54* (2006.01)
(52) U.S. Cl.
CPC ............ *C07D 209/54* (2013.01); *Y02P 20/55* (2015.11)
(58) Field of Classification Search
None
See application file for complete search history.

(56) References Cited

FOREIGN PATENT DOCUMENTS

CN   101759629 B   1/2012
CN   104557871 A   4/2015
(Continued)

OTHER PUBLICATIONS

International Search Report from PCT/CN2017/081893 dated Jul. 3, 2017.

*Primary Examiner* — Kamal A Saeed

(74) *Attorney, Agent, or Firm* — Warner Norcross + Judd LLP

(57) ABSTRACT

The present invention discloses a preparation method for efficient synthesis of sitafloxacin intermediate (7S)-5-azaspiro[2.4]heptane-7-yl-tert-butyl carbamate, comprising the following steps: reacting

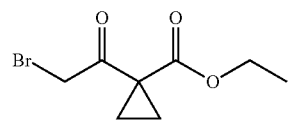

to obtain

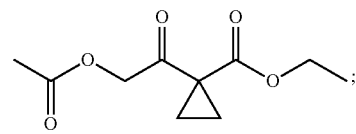

reacting

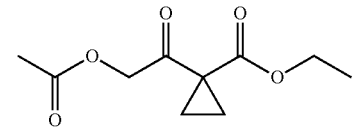

to obtain

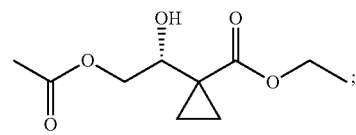

reacting to obtain (Continued)

and reacting

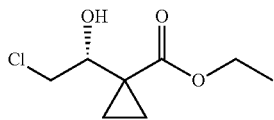

to obtain

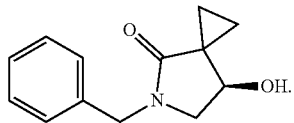

In the present invention, a single compound with a relatively high ee value can be obtained, the unnecessary waste of materials is avoided, the yield is significantly improved, the operation is simple, the industrial scale-up is easy, and the production cost is reduced.

10 Claims, 5 Drawing Sheets

(56) References Cited

FOREIGN PATENT DOCUMENTS

| | | |
|---|---|---|
| CN | 103360310 B | 3/2016 |
| CN | 104230790 B | 6/2016 |
| CN | 105906545 A | 8/2016 |
| CN | 104803857 B | 3/2017 |
| JP | H08157454 A | 6/1996 |

METHOD FOR PREPARING EFFICIENTLY SYNTHETIC SITAFLOXACIN INTERMEDIATE (7S)-5-AZASPIRO[2.4]HEPTANE-7-YL TERT-BUTYL CARBAMATE

FIELD OF THE INVENTION

The present invention relates to a preparation method for efficient synthesis of sitafloxacin intermediate (7S)-5-azaspiro[2.4]heptane-7-yl-tert-butyl carbamate.

BACKGROUND OF THE INVENTION

Sitafloxacin hydrate has the chemical name of 7-[(7S)-7-amino-5-azaspiro[2.4]hept-5-yl]-8-chloro-6-fluoro-1-[(1R,2S)-cis-2-fluorocyclopropyl]-1,4-dihydro-4-oxo-3-quinoline carboxylic acid, which is a broad-spectrum quinolones antibacterial agent developed by Daiichi Sankyo and the monohydrate thereof is used clinically for the treatment of severe refractory infectious diseases. This product can be developed for oral administration or injection administration. The oral quinolones drug Gracevit (sitafloxacin) (I) has come into the market of Japan, which is the first market on the world. The compensation price is set at 228 yen (US $2.17) per 50 mg tablet and the price of one pack of 10 fine granules is set at 576 yen.

This product has good pharmacokinetic properties, and can alleviate adverse physiological response, the antibacterial activity in vitro of which is significantly improved compared to most similar drugs. This product not only has significantly enhanced antibacterial activities against Gram-positive bacteria, but also has antibacterial activities against many clinically isolated strains resistant to fluoroquinolones. The study on the antibacterial activities of this product in vitro proves that this product has broad-spectrum antibacterial activities, i.e. it not only has antibacterial activities against Gram-negative bacteria, but also has strong antibacterial activities against Gram-positive bacteria (methicillin-resistant *staphylococcus aureus* and methicillin-resistant *staphylococcus epidermidis*), anaerobic bacteria (including *Bacteroides fragilis*) and mycoplasma, chlamydia, etc., in addition, this product has good bactericidal effect on many clinically common fluoroquinolones-resistant strains. This product is well absorbed orally, has a bioavailability of more than 70%, and can be distributed to extensive tissues, wherein the drug concentrations in various tissues outside the central nervous system are higher than the drug concentration in serum. Therefore, this product is expected to become an important drug for the treatment of single or mixed bacterial infections in respiratory tract, urogenital tract, abdominal cavity as well as skin soft tissues, etc.

(7S)-5-azaspiro[2.4]heptane-7-yl-tert-butyl carbamate is an important intermediate of sitafloxacin, whose disadvantages are that the synthetic route is long and difficult to be resolved, etc., resulting in limited market capacity, and high price.

At present, there are several methods for synthesizing (7S)-5-azaspiro[2.4]heptane-7-yl-tert-butyl carbamate:
The first method comprises the steps of synthesizing racemates and then resolving them to give one compound with single-configuration. This method results in the waste of the other chiral compound.

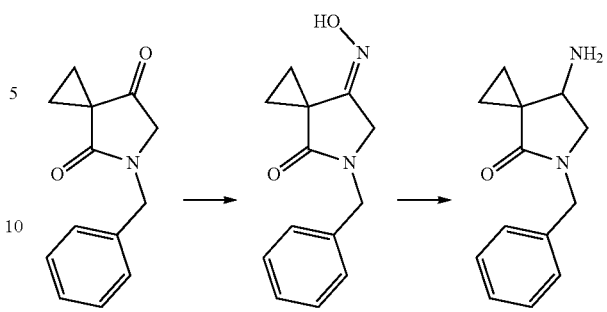

In the second method, dangerous chemicals such as cyanides or nitromethane are used, which poses a great safety risk in production and is inconvenient for scale-up production (CN101544581A).

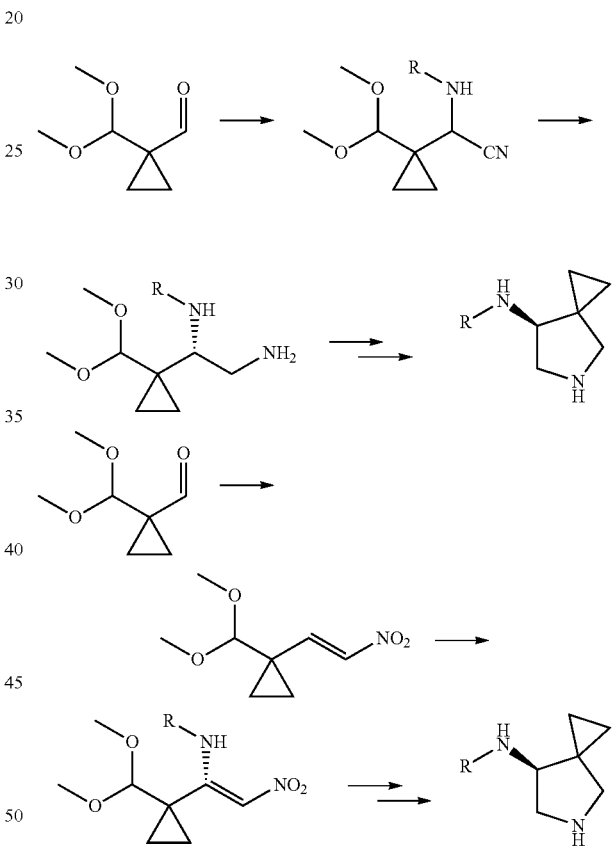

In the third method, a catalyst is used for reducing to directly obtain chiral amines, however, the reduction efficiency is still not high, and the ee value is only 53% (JP2004099609A).

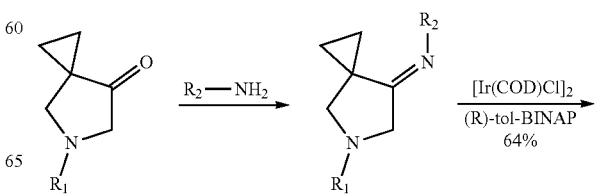

-continued

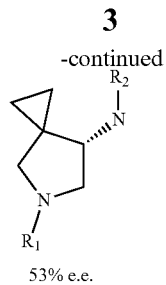

53% e.e.

In the fourth method, a beer yeast is used for reducing so as to obtain the chiral alcohols, and then Mitsunobu reaction is performed to obtain the chiral amines. This method has low reduction efficiency in volume and is difficult for scale-up production (Chem. Pharm. Bull. 1998, 46, 587).

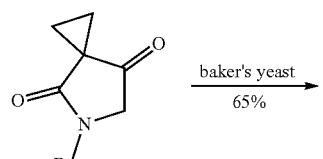

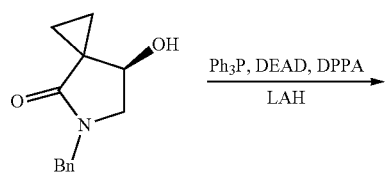

98% ee

The disadvantages of these methods are that it is difficult for scale-up production, resulting in that there is a very few manufacturers for producing (7S)-5-azaspiro[2.4]heptane-7-yl-tert-butyl carbamate, and the price is very high, which seriously hinder the further application and development thereof in organic chemistry and biomedicine. Therefore, it will have a great practical value to develop a process route that can be safely scaled up.

SUMMARY OF THE INVENTION

The present invention aims to provide a preparation method for efficient synthesis of sitafloxacin intermediate (7S)-5-azaspiro[2.4]heptane-7-yl-tert-butyl carbamate.

The technical solution adopted by the present invention is: A preparation method for efficient synthesis of sitafloxacin intermediate (7S)-5-azaspiro[2.4]heptane-7-yl-tert-butyl carbamate comprises the following steps:

1) fully reacting

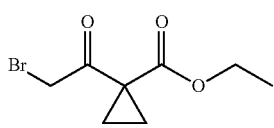

with acetic acid and potassium acetate to obtain

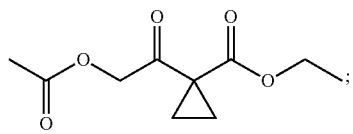

2) subjecting

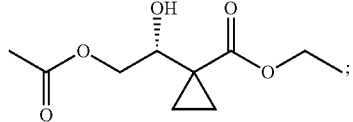

to Noyori hydrogenation reaction to obtain

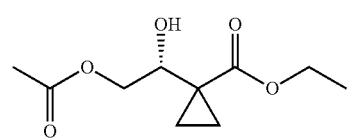

3) fully reacting

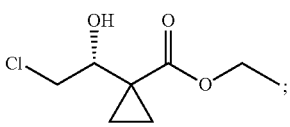

with a solution of hydrochloric acid in ethanol to obtain

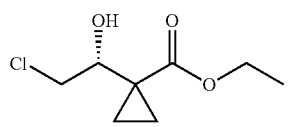

4) in the presence of cesium carbonate, subjecting

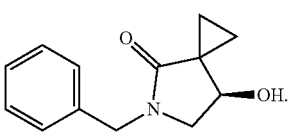 [SMILES: O=C1N(Cc2ccccc2)C[C@H](O)C12CC2]

and benzylamine to cyclization reaction in a solvent to obtain

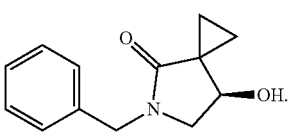 [SMILES: O=C1N(Cc2ccccc2)C[C@H](O)C12CC2]

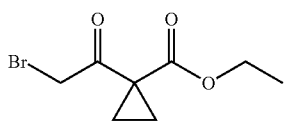

is obtained through the following steps:

① in the presence of a base, fully reacting

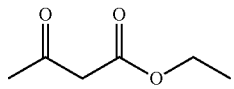

with 1,2-dibromoethane in an organic solvent to obtain

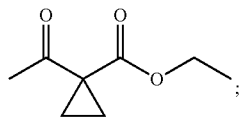

① subjecting

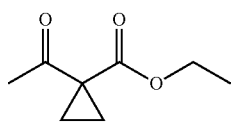

and Br₂ to substitution reaction in an organic solvent to obtain

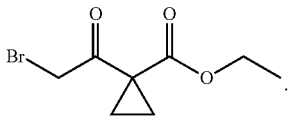

It further comprises the following steps:

5) In the presence of DEAD and trialkylphosphine and/or triarylphosphine, reacting

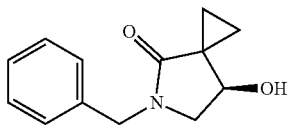 [SMILES: O=C1N(Cc2ccccc2)C[C@H](O)C12CC2]

with DPPA to obtain

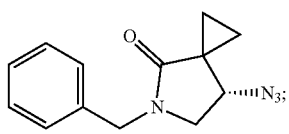 [SMILES: [N-]=[N+]=N[C@@H]1CN(Cc2ccccc2)C(=O)C12CC2]

6) reducing the azide group of

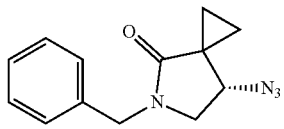 [SMILES: [N-]=[N+]=N[C@@H]1CN(Cc2ccccc2)C(=O)C12CC2]

into primary amine group to obtain

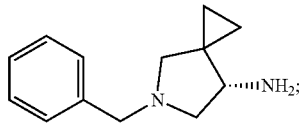 [SMILES: N[C@@H]1CN(Cc2ccccc2)CC12CC2]

7) grafting the primary amine group of

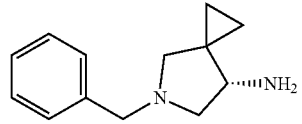 [SMILES: N[C@@H]1CN(Cc2ccccc2)CC12CC2]

with a BOC protecting group to obtain

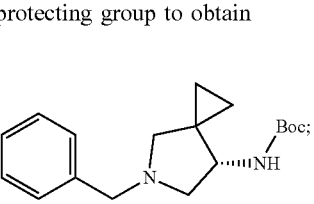

8) reducing

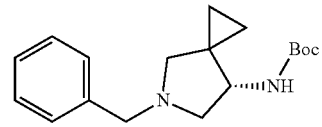 [SMILES: CC(C)(C)OC(=O)N[C@@H]1CN(Cc2ccccc2)CC12CC2]

to obtain

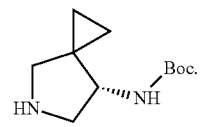

In step 1), the usage ratio of

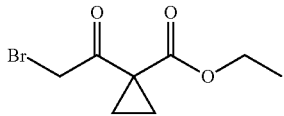

to acetic acid and potassium acetate is in the range of 1 g:(3-5) mL:(1.25-1.5) g.

In step 2), the catalyst used for the Noyori hydrogenation reaction is Ru-BINAP.

In step 3), the mass ratio of

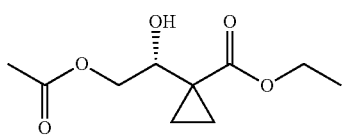

to the HCl in the solution of hydrochloric acid in ethanol is in the range of 1:(3.5-4).

In step 4), the mass ratio of

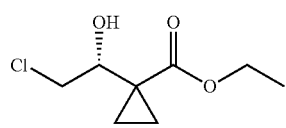

to benzylamine is 1:(0.15-0.2).

In step 5), the usage ratio of

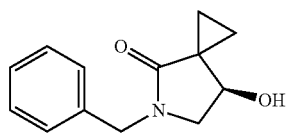 [SMILES: O=C1N(Cc2ccccc2)C[C@H](O)C12CC2]

to DPPA is 1:(1.5-2).

In step 6), the reducing agent used for the reduction is sodium borohydride or lithium aluminum hydride.

In step 8), the reducing agent used for the reduction is Pd/C.

The beneficial effects of the present invention are as follows:

In the present invention, a single compound with a relatively high ee value can be obtained, the unnecessary waste of materials may be avoided, the yield may be significantly improved, the operation may be simple, the industrial scale-up may be easy, and the production cost may be reduced.

DETAILED DESCRIPTION OF THE EMBODIMENTS

Figure 1:
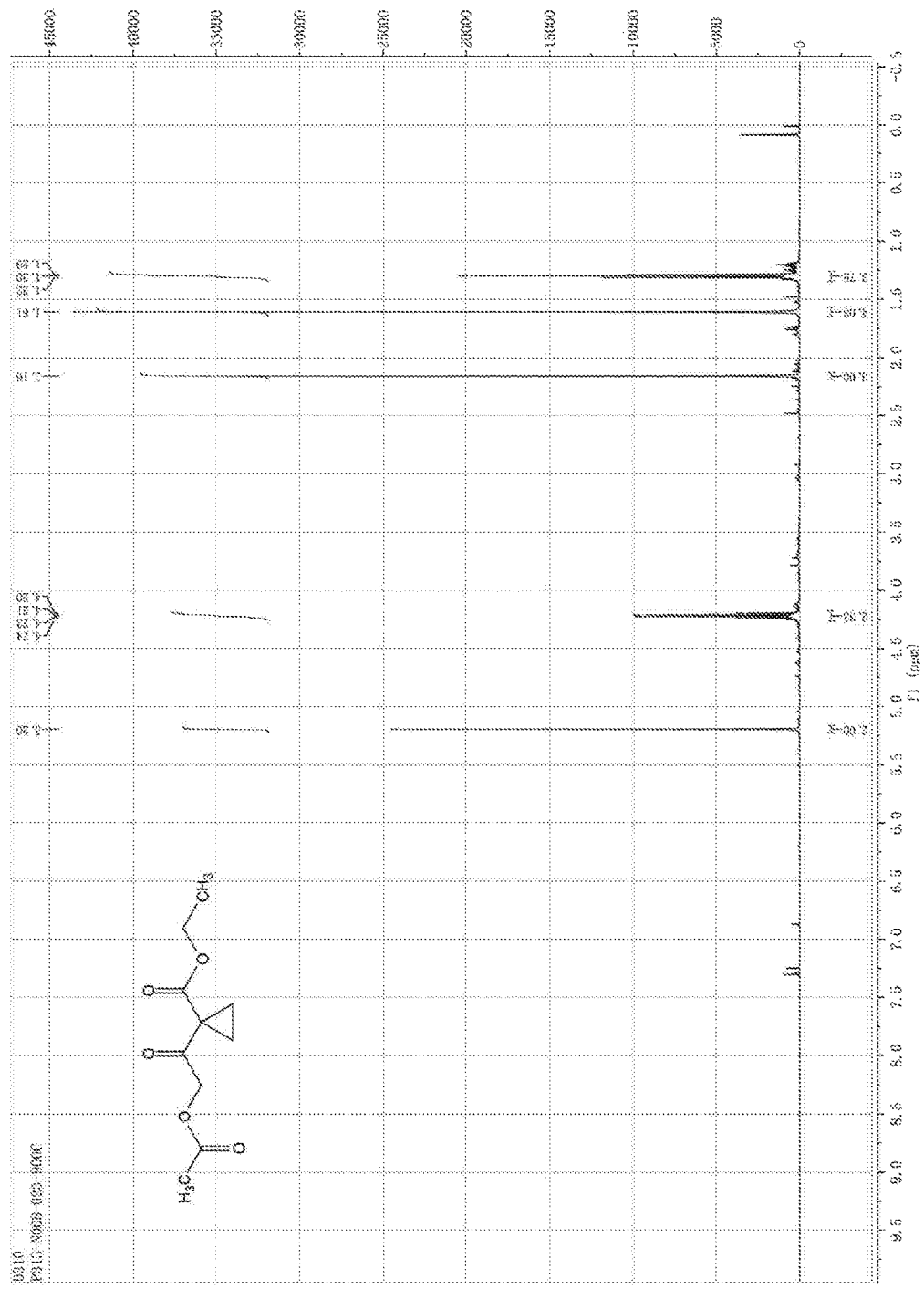
FIG. 1 shows the HNMR spectrum of compound 3.

The synthesis route of the present invention is illustrated as follows:

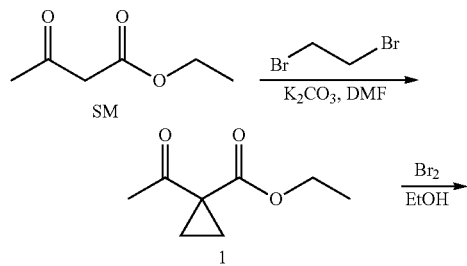

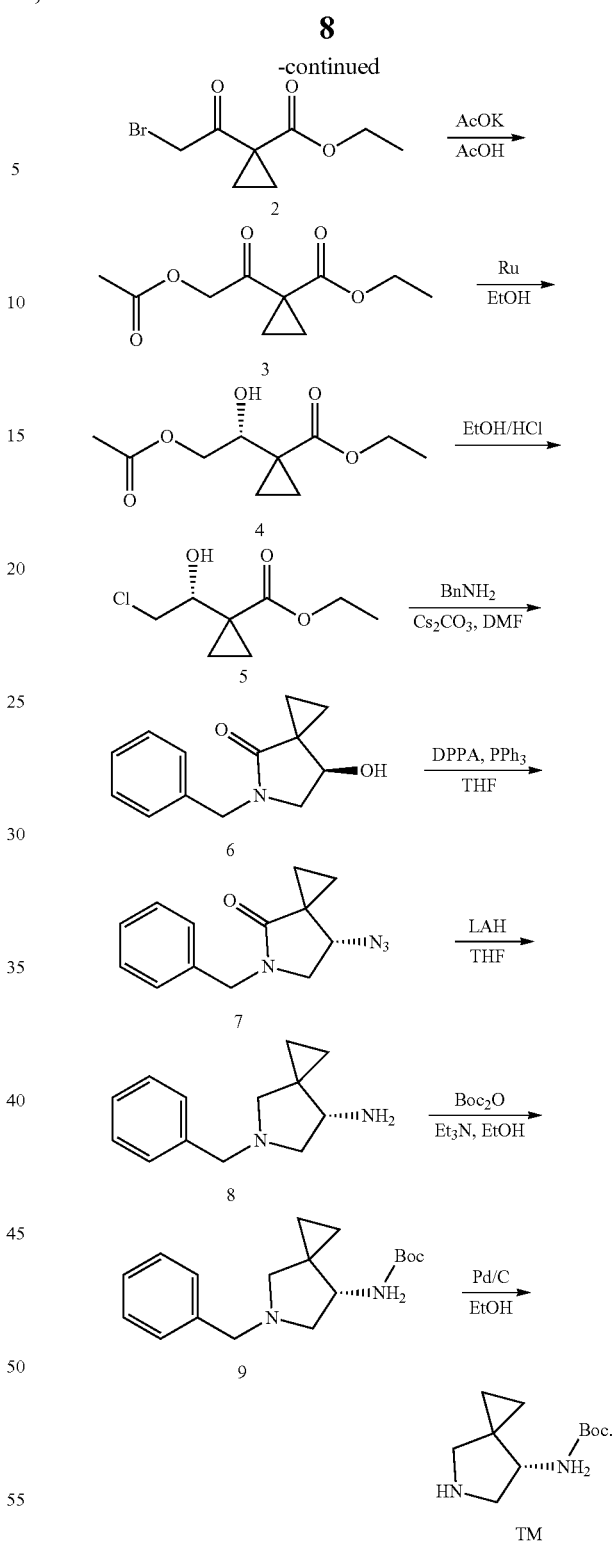

The present invention will be further described below in combination with specific Examples.

Example 1

The First Step:

13.0 g of ethyl acetoacetate was added to a 250 mL reaction flask, then 130 mL of DMF, 37.6 g of 1,2-dibromoethane, and 52.44 g of potassium carbonate were added thereto in sequence, the mixture was stirred and reacted overnight, then 650 mL of water was added thereto. The resulting solution was extracted with ethyl acetate, dried, concentrated and distilled to obtain 13.0 g of compound 1.

The Second Step:
13.0 g of compound 1 was added to a 250 mL three-necked flask, and 130 mL of ethanol was added thereto, then 16.0 g of $Br_2$ was added dropwise thereto under the condition of ice bath. After finishing the addition of $Br_2$, the mixture was stirred at room temperature for 2 hours. The mixture was added to 400 mL of water and then separated to obtain the lower layer as the product layer, which was concentrated to obtain 15.0 g of compound 2.

The Third Step:
15.0 g of compound 2 was added to a 250 mL three-necked flask, 50 mL of acetic acid and 18.8 g of potassium acetate were added thereto, the mixture was stirred, and the system was heated to 70° C. overnight. After cooled, the system was added into 200 mL of water, extracted three times with ethyl acetate, dried, concentrated, and distilled to obtain 10.0 of compound 3. The HNMR spectrum of compound 3 was shown in FIG. 1.

Figure 2:
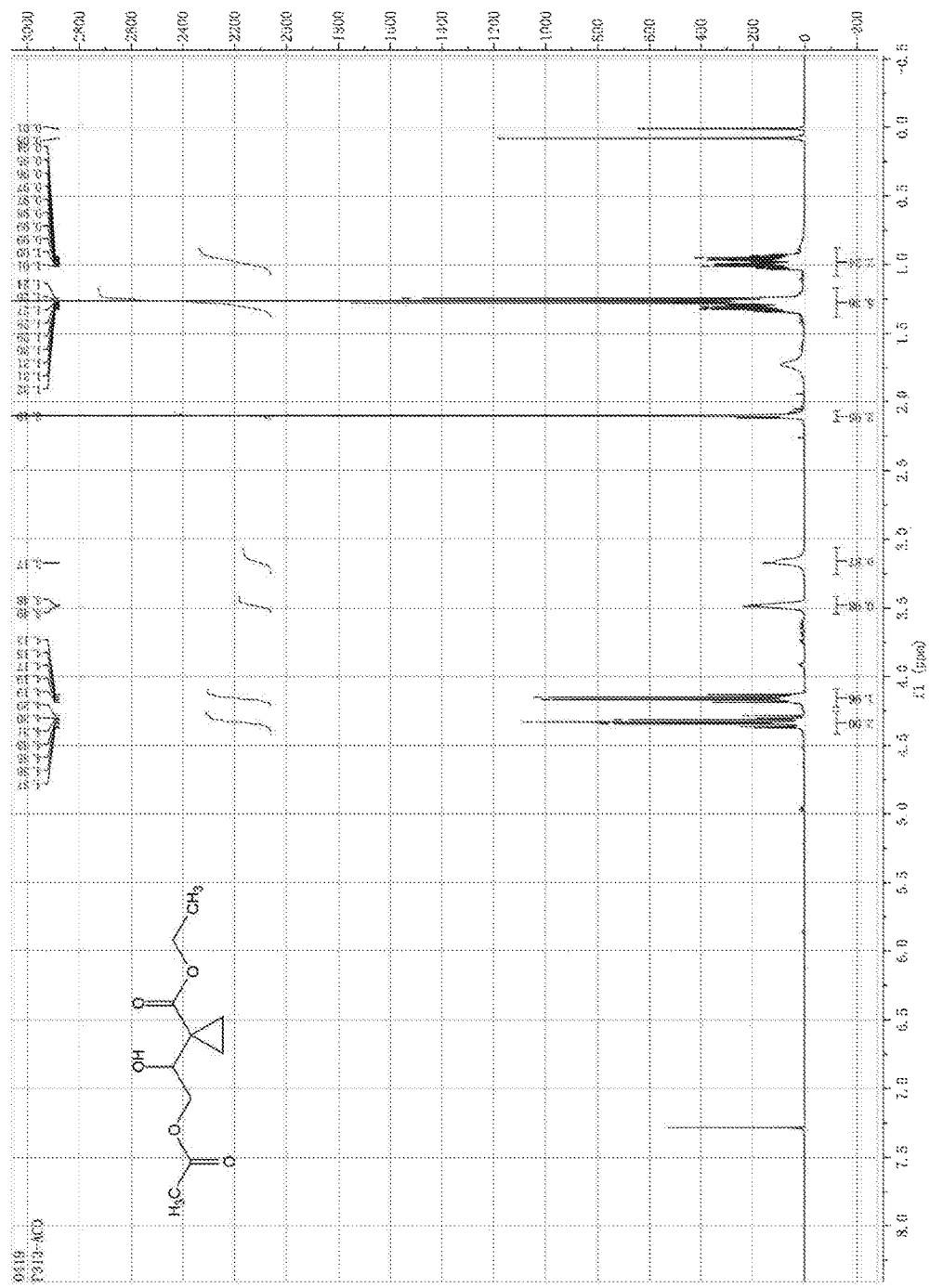
FIG. 2 shows the HNMR spectrum of compound 4.

The Fourth Step:
10.0 g of compound 3 was added into a 250 mL autoclave, 100 mL of anhydrous ethanol was added thereto, nitrogen bubbling was performed for 10 minutes, 0.1 g of Ru-BINAP was added, and nitrogen bubbling was continued for 10 minutes, the autoclave was screwed on, and replaced with hydrogen three times, the mixture was reacted at a pressure of 0.5 MPa and a temperature of 100° C. overnight. After concentration, 10.0 g of compound 4 was obtained (ee. 98.6%), HNMR spectrum of which was shown in FIG. 2.

Figure 3:
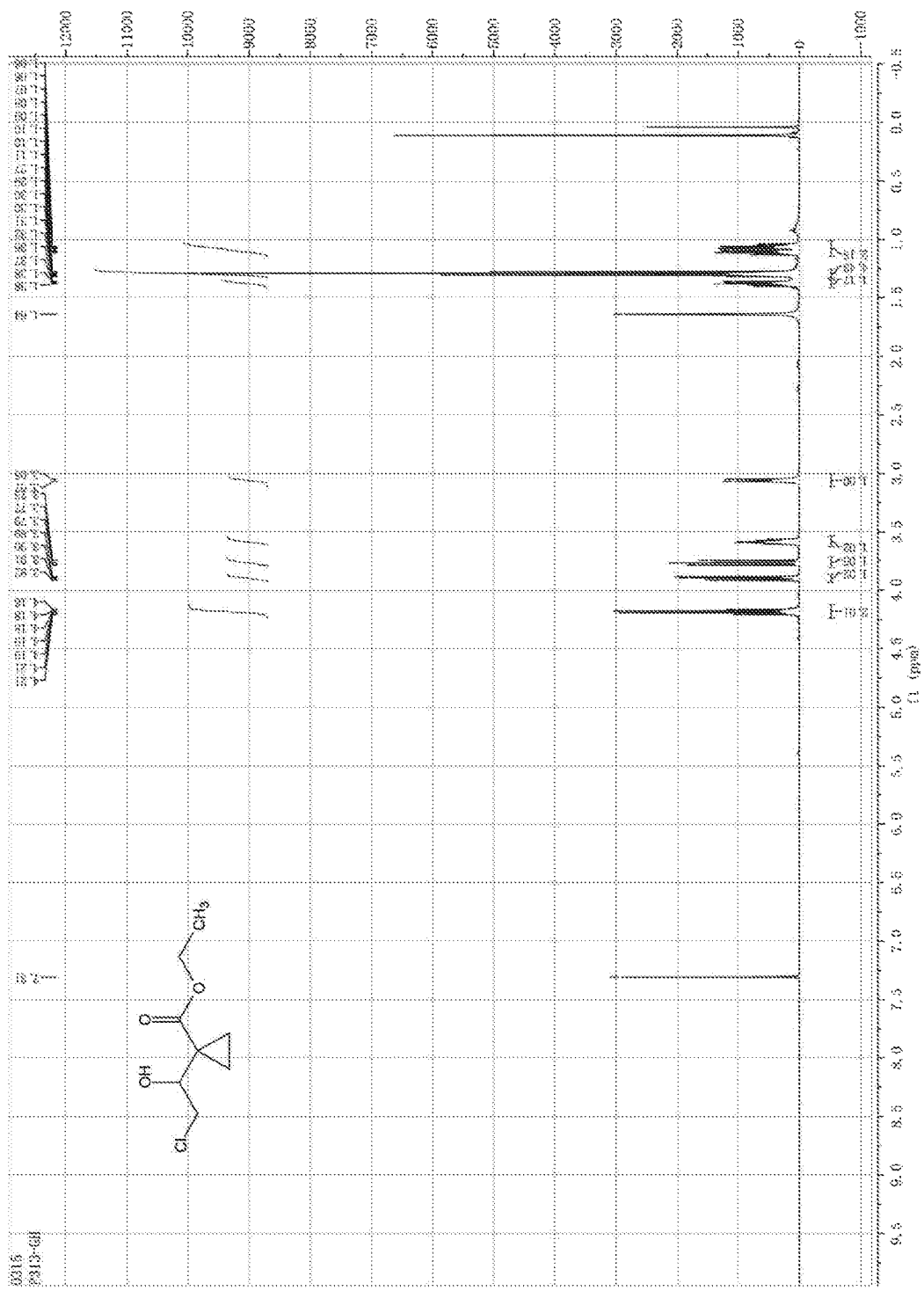
FIG. 3 shows the HNMR spectrum of compound 5.

The Fifth Step:
10.0 g of compound 4 was added to a 250 mL three-necked flask, and 100 mL of 10N HCl EtOH was added thereto, the mixture was heated and refluxed overnight, concentrated to obtain 8.0 g of compound 5 (ee. 98.5%). The HNMR spectrum of compound 5 was shown in FIG. 3.

Figure 4:
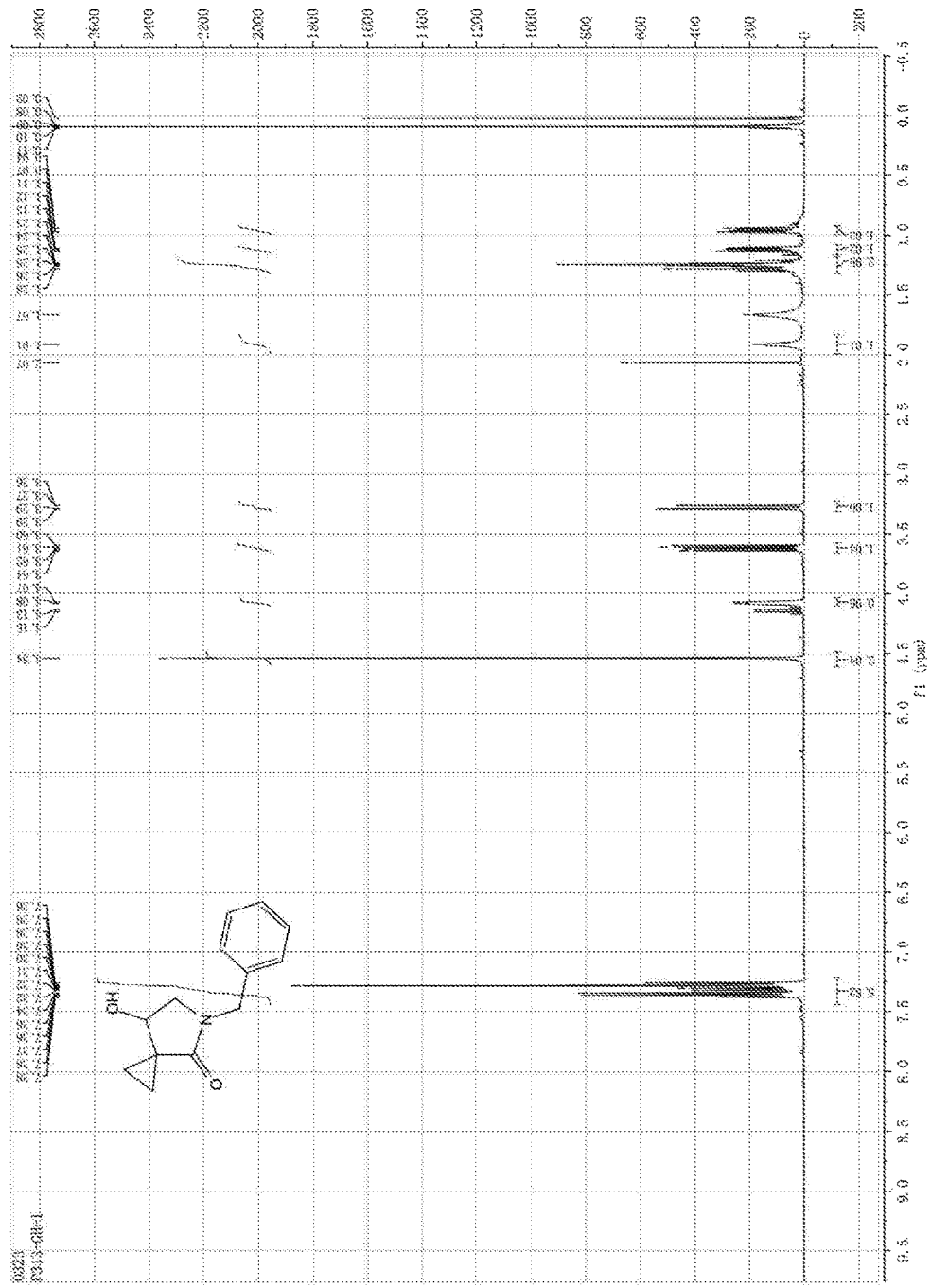
FIG. 4 shows the HNMR spectrum of compound 6.

The Sixth Step:
8.0 g of compound 5 was added to a 250 mL three-necked flask, then 27.0 g of cesium carbonate, 5.3 g of benzylamine and 100 mL of DMF were added thereto in sequence, the mixture was heated to 100° C. overnight, cooled to room temperature, and added to 500 mL of water. The resulting solution was extracted with ethyl acetate, dried and concentrated to obtain 3.0 g of compound 6 (ee. 98.5%). The HNMR spectrum of compound 6 was shown in FIG. 4.

The Seventh Step:
3.0 g of compound 6 was added to a 100 mL three-necked flask, 40 mL of tetrahydrofuran, 4.3 g of triphenylphosphine and 4.6 g of DPPA were added thereto in sequence, 2.9 g of DEAD was added dropwise thereto under the condition of nitrogen atmosphere and ice bath. After the addition was completed, the ice bath was removed and the mixture was stirred at room temperature overnight, then it was concentrated and purified by column to obtain 2.0 g of compound 7 (ee. 98.4%).

The Eighth Step:
2.0 g of lithium aluminium tetrahydride was suspended in 40 mL of anhydrous tetrahydrofuran, and 5 mL of a tetrahydrofuran solution containing 2.0 g of compound 7 was slowly added thereto under an ice bath, and then the mixture was heated to reflux overnight. The reaction was quenched according to a standard procedure. The resulting solution was filtered, and concentrated to obtain 1.0 g of compound 8 (ee. 98.2%).

Figure 5:
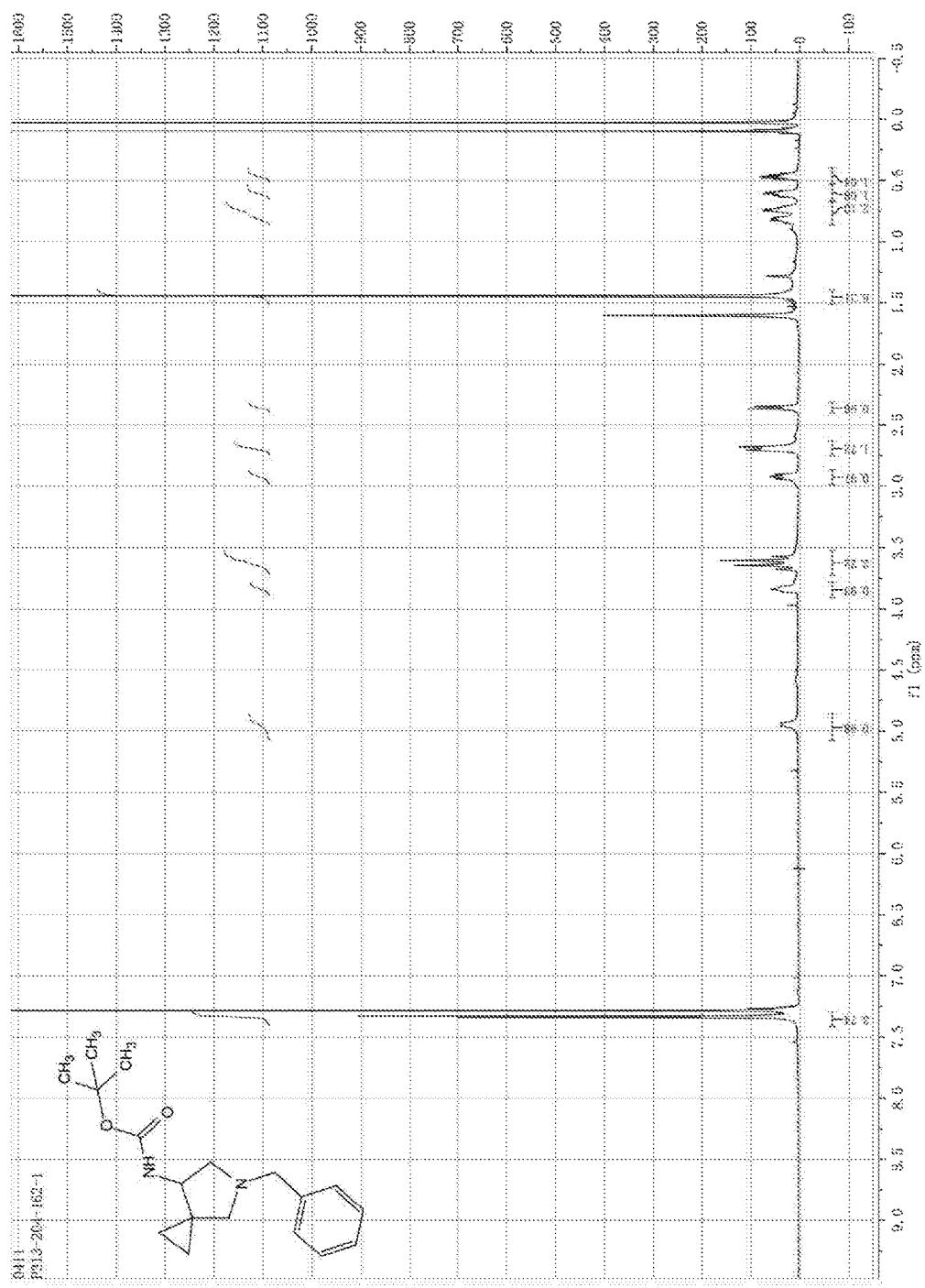
FIG. 5 shows the HNMR spectrum of compound 9.

The Ninth Step:
1.0 g of compound 8 was added to a 50 mL single-necked flask, then 10 mL of ethanol, 1.0 g of triethylamine and 1.6 g of $Boc_2O$ were added thereto in sequence, the mixture was stirred at room temperature overnight and concentrated. Then ethyl acetate was added, the obtained mixture was washed with citric acid solution, sodium bicarbonate solution and saturated saline solution successively, dried and concentrated to obtain 1.4 g of compound 9 (ee. 98.2%). The HNMR spectrum of compound 9 was shown in FIG. 5.

The Tenth Step:
1.4 g of compound 9 was added to a 50 mL single-necked flask, then 0.15 g of Pd/C and 15 mL of ethanol were added thereto, the flask was replaced with hydrogen three times. The mixture was stirred at room temperature under a hydrogen atmosphere overnight, filtered, and concentrated to obtain 0.9 g (ee. 98.3%) of the final product.

What is claimed is:

1. A method of preparing for efficient synthesis of sitafloxacin intermediate (7S)-5-azaspiro[2.4]heptane-7-yl-tert-butyl carbamate, comprising the following steps:

1) reacting

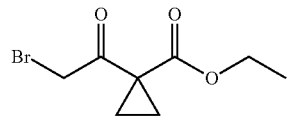

with acetic acid and potassium acetate to obtain

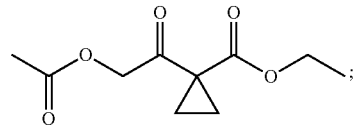

2) subjecting

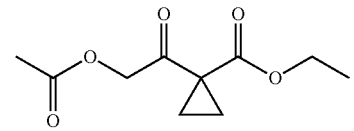

to Noyori hydrogenation reaction to obtain

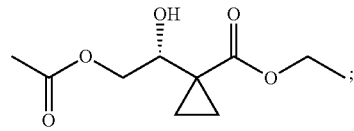

3) reacting

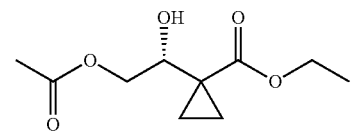

with a solution of hydrochloric acid in ethanol to obtain

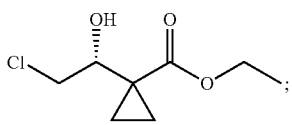

4) in the presence of cesium carbonate, subjecting

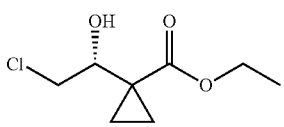

and benzylamine to cyclization reaction in a solvent to obtain

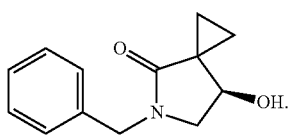 [SMILES: O=C1N(Cc2ccccc2)C[C@H](O)C12CC2]

2. The method of preparing for efficient synthesis of sitafloxacin intermediate (7S)-5-azaspiro[2.4]heptane-7-yl-tert-butyl carbamate according to claim 1, wherein

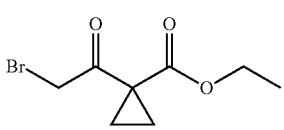

is obtained through the following steps:
① in the presence of a alkali, reacting

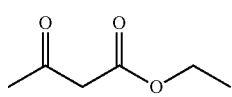

with 1,2-dibromoethane in an organic solvent to obtain

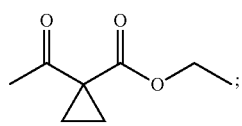

② subjecting

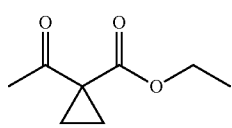

and Br$_2$ to substitution reaction in an organic solvent to obtain

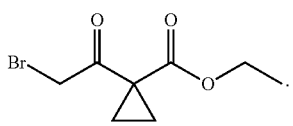

3. The method of preparing for efficient synthesis of sitafloxacin intermediate (7S)-5-azaspiro[2.4]heptane-7-yl-tert-butyl carbamate according to claim 1, further comprising the following steps:
5) in the presence of DEAD and trialkylphosphine and/or triarylphosphine, reacting

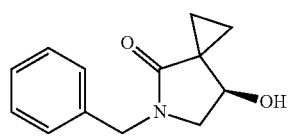 [SMILES: O=C1N(Cc2ccccc2)C[C@H](O)C12CC2]

with DPPA to obtain

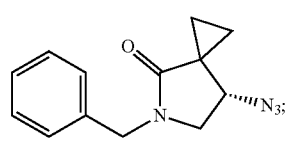 [SMILES: [N-]=[N+]=N[C@@H]1CN(Cc2ccccc2)C(=O)C12CC2]

6) reducing the azide group of

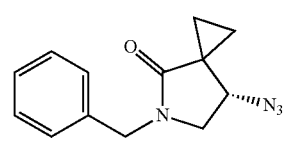 [SMILES: [N-]=[N+]=N[C@@H]1CN(Cc2ccccc2)C(=O)C12CC2]

to primary amine to obtain

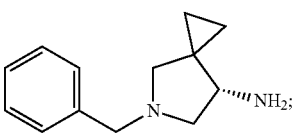 [SMILES: N[C@@H]1CN(Cc2ccccc2)CC12CC2]

7) grafting the primary amine of

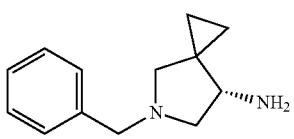 [SMILES: N[C@@H]1CN(Cc2ccccc2)CC12CC2]

with BOC protecting group to obtain

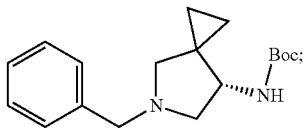 [SMILES: CC(C)(C)OC(=O)N[C@@H]1CN(Cc2ccccc2)CC12CC2]

8) reducing

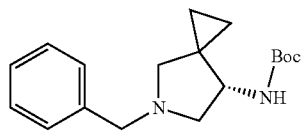 [SMILES: CC(C)(C)OC(=O)N[C@@H]1CN(Cc2ccccc2)CC12CC2]

to obtain

4. The method of preparing for efficient synthesis of sitafloxacin intermediate (7S)-5-azaspiro[2.4]heptane-7-yl-tert-butyl carbamate according to claim 1, wherein in step 1), the usage ratio of

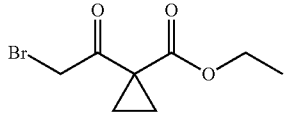

to acetic acid and potassium acetate is 1 g:(3-5) mL:(1.25-1.5) g.

5. The method of preparing for efficient synthesis of sitafloxacin intermediate (7S)-5-azaspiro[2.4]heptane-7-yl-tert-butyl carbamate according to claim 1, wherein in step 2), the catalyst used for the Noyori hydrogenation reaction is Ru-BINAP.

6. The method of preparing for efficient synthesis of sitafloxacin intermediate (7S)-5-azaspiro[2.4]heptane-7-yl-tert-butyl carbamate according to claim 1, wherein in step 3), the mass ratio of

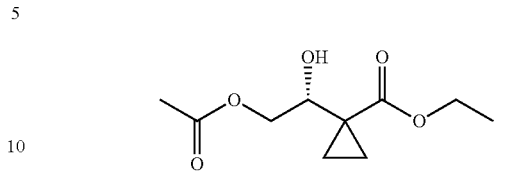

to the HCl in the solution of hydrochloric acid in ethanol is 1:(3.5-4).

7. The method of preparing for efficient synthesis of sitafloxacin intermediate (7S)-5-azaspiro[2.4]heptane-7-yl-tert-butyl carbamate according to claim 1, wherein in step 4), the mass ratio of

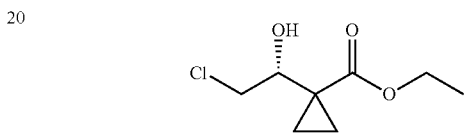

to benzylamine is 1:(0.15-0.2).

8. The method of preparing for efficient synthesis of sitafloxacin intermediate (7S)-5-azaspiro[2.4]heptane-7-yl-tert-butyl carbamate according to claim 3, wherein in step 5), the usage ratio of

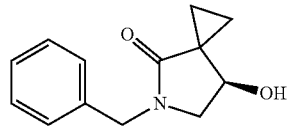 [SMILES: O=C1N(Cc2ccccc2)C[C@H](O)C12CC2]

to DPPA is 1:(1.5-2).

9. The method of preparing for efficient synthesis of sitafloxacin intermediate (7S)-5-azaspiro[2.4]heptane-7-yl-tert-butyl carbamate according to claim 3, wherein in step 6), the reducing agent used for the reduction is sodium borohydride or lithium aluminum hydride.

10. The method of preparing for efficient synthesis of sitafloxacin intermediate (7S)-5-azaspiro[2.4]heptane-7-yl-tert-butyl carbamate according to claim 3, wherein in step 8), the reducing agent used for the reduction is Pd/C.

* * * * *